(12) United States Patent
Pleckham

(10) Patent No.: US 10,791,705 B1
(45) Date of Patent: Oct. 6, 2020

(54) AIR CUSHION DEVICE, SYSTEM AND METHOD FOR DETERMINING LAMENESS AND WEIGHT MONITORING

(71) Applicant: Gerald A. Pleckham, Matteson, IL (US)

(72) Inventor: Gerald A. Pleckham, Matteson, IL (US)

( * ) Notice: Subject to any disclaimer, the term of this patent is extended or adjusted under 35 U.S.C. 154(b) by 0 days.

(21) Appl. No.: 16/890,478

(22) Filed: Jun. 2, 2020

Related U.S. Application Data

(60) Provisional application No. 62/905,611, filed on Sep. 25, 2019.

(51) Int. Cl.
A01K 1/015 (2006.01)
A01K 1/10 (2006.01)
G01L 5/16 (2020.01)
G01G 17/08 (2006.01)

(52) U.S. Cl.
CPC .............. A01K 1/105 (2013.01); A01K 1/015 (2013.01); G01G 17/08 (2013.01); G01L 5/16 (2013.01)

(58) Field of Classification Search
CPC ............................... A01K 1/015; A01K 1/0157
See application file for complete search history.

(56) References Cited

U.S. PATENT DOCUMENTS

| 4,195,643 | A | | 4/1980 | Pratt, Jr. |
| 6,119,530 | A | | 9/2000 | Oddsson et al. |
| 6,152,077 | A | * | 11/2000 | Bristow ................ A01K 1/015 119/28.5 |
| 6,699,207 | B2 | | 3/2004 | Tasch et al. |
| 9,186,091 | B2 | | 11/2015 | Mainini et al. |
| 9,636,046 | B2 | | 5/2017 | Tasch |
| 9,788,758 | B2 | | 10/2017 | Heo et al. |
| 2005/0076855 | A1 | * | 4/2005 | Throndsen ........... A01K 1/0157 119/526 |
| 2010/0023293 | A1 | | 1/2010 | Walthert |
| 2010/0056960 | A1 | | 3/2010 | Lanny |
| 2010/0210974 | A1 | | 8/2010 | Brett et al. |
| 2015/0090184 | A1 | * | 4/2015 | Wasuck ............... A01K 1/0157 119/28.5 |
| 2018/0177449 | A1 | | 6/2018 | Latey |
| 2020/0120895 | A1 | * | 4/2020 | Wasuck ............... A47C 27/081 |

* cited by examiner

Primary Examiner — Monica L Barlow
(74) Attorney, Agent, or Firm — Charles S. Sara; Erin E. Block; DeWitt LLP

(57) ABSTRACT

The present invention relates to a farming/veterinary device, system, and method for sensing force to analyze the stance of an animal or human to determine lameness and total weight monitoring. The invention is directed to an air cushion device for determining lameness and total weight management for animals with an air cushion for each animal leg which will enable the system to determine the force exerted on each air cushion. Optimally, the air cushion device is waterproof. The system is directed to incorporating the air cushion device with an air supply system and sensor system to automatically determine lameness and total weight in animals. The method is directed to a procedure for using the air cushion system to determine lameness and total weight in animals. Because implementations of the device are waterproof, it is suitable for use in any type of wet or dirty environment. Further, due to making the determinations while the animal is standing still, the device is capable of on-site installation in areas of the farm such as milking stalls, cattle chutes, and other small areas in which the animal is used to being.

20 Claims, 8 Drawing Sheets

AIR CUSHION DEVICE, SYSTEM AND METHOD FOR DETERMINING LAMENESS AND WEIGHT MONITORING

CROSS-REFERENCE TO RELATE APPLICATIONS

The present application claims priority to U.S. Provisional Patent Application No. 62/905,611, filed Sep. 25, 2019, the content of which is incorporated herein by reference in its entirety.

FIELD OF THE INVENTION

The present invention relates a farming/veterinary device, system and method for sensing force to analyze the stance of an animal or human to determine lameness and total weight monitoring.

BACKGROUND

It is often desirable to determine if an animal or person has a foot/leg ailment causing lameness in the animal/person. Lameness in animals can lead to weight loss and subpar performance by the animal. For example, a dairy cow with a lame leg may start to refuse feed and lose weight, which may result in a diminishing of milk received from the dairy cow.

Therefore, it is desirable to determine lameness and weight loss in animals as soon as possible to address the issue prior to the lameness causing subpar performance from the animal. Further, it is desirable to be able to regularly monitor the condition until it resolves to ensure treatment is effective.

Traditionally, lameness has been determined by veterinarians or other experts who observe the animal walk, visually analyze the animal's gait, and perform a physical inspection of the animal. Recently, efforts have been made to improve on the traditional observational methods through the use of sensor technology. These efforts include measuring the gait and forces from the feet/hooves of animals/people as they walk to determine lameness and other ailments. Most of these efforts have implemented force plate technology with numerous sensors that can detect how the animal/human moves across the plates and the force exerted by each foot/hoof.

For example, U.S. Pat. No. 6,699,207 to Tasch et al. (the '207 patent) discloses a method and apparatus for detecting lameness in animals. The system and method of the '207 patent discloses a computerized diagnostic system that includes two force plates with a plurality of sensors to detect ground reaction forces produced by an animal as the animal passes through the device. The data gathered by the sensors can be compiled to determine the magnitude and location of a force applied to each plate. Ideally, the plates will be longer than the animal's normal gait and include step-up and step-down sections that do not include sensors. Accordingly, the apparatus must be relatively large in comparison to the size of the animal in order to allow the system to determine the forces exerted by the animal as it walks.

A number of patents have implemented systems that do not require such a significant structure to analyze the gait of an animal in order to determine lameness in the animal. For example, U.S. Pat. No. 4,195,643 to Pratt, Jr. (the '643 patent) discloses force plate technology to measure forces generated by bodies at rest and in motion using one or more force plates with multiple sensors. The '643 patent discloses determining lameness in a person or animal through determining the nature of the impact of the limb on the force plate. Another example is U.S. Pat. No. 6,119,530 to Oddsson et al. (the '530 patent) which discloses a force sensing device to determine the force exerted, both perpendicular to the device and parallel to the device, for use in analyzing the movement of a person or animal. The '530 patent has a force sensing plate that is suspended in a frame on bearings, allowing the plate to move within the frame when it is stepped on. The outside perimeter of the frame also contains sensors to determine the horizontal force caused when a person or animal steps onto the plate. However, these devices all require measuring the force of the animal/human while in motion to determine lameness. Requiring the animal or human to be in motion to determine lameness, requires additional space and setup for the apparatus to be used to enable the animal to step onto and possibly traverse through the apparatus. Further, if the movement of the animal or human is not natural, the reading may not accurately detect the ailment or lameness.

The above patents all require the analysis of an animal in motion to determine lameness. This means the device must be installed in an area with sufficient room for the animal to step onto and across the device. Further, none of the devices in the above patents disclose being waterproof or capable of use in a wet environment. Due to the space requirements and environmental conditions of most animal farms, these devices may not be practical to install at the farm. This means that either the farmer would need to transport any animals of concern to a location that has a system installed or that the system would need to be portable and capable of temporary installation at the farm. In either circumstance it would be impractical for the farmer to be able to frequently use the device to determine lameness and monitor the condition in order to detect the issue before the animal exhibits subpar performance.

Further, even if a farm were able to permanently install and implement one of the above devices, the accuracy of the determination is questionable. Due to the space required and environmental conditions on a farm, the device likely could not be installed in a space the animals are normally kept. This takes additional time and effort for the farmer to use.

U.S. Pat. No. 9,186,091 to Mainini et al. (the '091 patent) has attempted to overcome this issue. The '091 patent discloses a system and method for analyzing the stance of animals to determine the distribution of weight of an animal to detect and treat problems such as stability, lameness, or other ailments. The device and method of the '091 patent disclose having the animal stand with each foot/hoof on a sensor region to take sensor readings from each sensor region. When determining lameness on an animal that is standing still, the more still the animal is, the more accurate the readings and determinations. The '091 patent discloses including a food holder and a fence around the perimeter of the device to help stabilize the animal.

However, the fence and food holder are added to the device and are not necessarily the elements the animal would be used to having around them. Animals, particularly farm animals, will be most stable and still in an environment they are used to and conditions where they are comfortable. Further, the device in the '091 patent does not lend itself to being installed in a farm environment. The elements of water and dirt in the farm environment would likely cause the device to either malfunction or become inaccurate.

SUMMARY OF THE INVENTION

An ideal system and method for determining lameness would be a device capable of determining lameness and the total weight of an animal while the animal is standing in a still position on the device. Further, the device would be installable on-site in a convenient environment where the animal is accustomed and comfortable. This type of device and method would allow the user to regularly test for lameness and weight management without the inconvenience of having to transport the animals to a different location. Additionally, this type of device would also be able to operate in wet, dirty, and suboptimal environments without decreased accuracy.

The above-noted problems are overcome by the present invention. The present invention is directed to a waterproof/environment proof device and method for determining lameness and total weight management in animals. Specifically, the device can be installed on-site at the location of the animals regardless of the environment conditions. For example, the device can be installed in milking stalls for dairy cows and the method performed while milking occurs.

Lameness occurs in cows and other animals for a number of reasons including when they have been injured, which can sometimes be undetectable with a visual inspection. When an animal is lame or has been injured, it will transfer weight unevenly to the uninjured feet. By measuring the weight from each individual foot from each quarter, a determination can be made in regard to lameness and may provide early detection of issues affecting the animal. By adding the weight from each foot, the total weight can be determined, and the weight of the animal can be managed. Early detection of an injury and/or lameness allows the farmer to treat the problem as soon as possible, which can minimize the impact of the injury on the animal's performance.

The invention is directed to an air cushion device for determining lameness and total weight management for animals. The air cushion device may be constructed to be waterproof/environment proof. The air cushion device includes a plurality of air cushions. Each air cushion is connected to an incoming air line and a data air line. The incoming air lines supply the air cushions with air and the data air lines supply the force being exerted on the air cushions once inflated.

In an embodiment, the air cushion device includes a plurality of air cushions, a plurality of incoming air lines and a plurality of data air lines. Each air cushion includes a top member and a bottom member connected by an airtight seal between the top member and the bottom member along a perimeter of the air cushion. Each air cushion further includes an expandable air pocket formed in the air cushion by the airtight seal. Each air cushion is configured to receive at least a portion of an animal on the top member. The expandable air pocket of each air cushion is connected to an incoming air line and a data air line. Each incoming air line is connected to the expandable air pocket of one of the plurality of air cushions. The incoming air lines supply each air cushion with a supply of air to inflate each air cushion. Each data air line is connected to the expandable air pocket of one of the plurality of air cushions. The data air lines supply a force being exerted on each of the plurality of air cushions once the air cushions are inflated.

The invention is further directed to an air cushion system for determining lameness and total weight management for animals. The system includes an air cushion device, an air supply system, and sensors. The air supply system provides air to the air cushions to inflate them. The sensors determine the force being exerted on the air cushions once inflated. The sensors may be physically or remotely (via a network or Wi-Fi) connected to a computation device. Optionally, the sensor may not be connected to the computing device and sensor data is collected from the sensors and input into a computation device that is separate from the system. The computation device uses the sensor data to determine lameness and total weight for the animal.

In one version, the air cushion system includes an air cushion device as described above, an air supply system and a plurality of sensors. The air supply system is connected to the plurality of incoming air lines of the air cushion device. The air supply system includes an air supply to provide air to the air cushion device. The plurality of sensors are connected to the plurality of data air lines of the air cushion device to determine the force being exerted on the air cushions. The number of sensors equals the number of data air lines such that the sensors are connected to the data air lines on a one-to-one basis.

The invention is further directed to a method for determining lameness and total weight for animals. In the method, an air cushion system is installed at a location. The animal is positioned on the air cushion device with each air pillow having one animal foot on it. The animal is secured, and the air cushion device is inflated by the air control system. The sensors determine the force being exerted on each air cushion and the force data is supplied to the computing device. The computing device uses the force data to determine lameness and total weight of the animal. The air cushion device is deflated, and the animal is removed from the air cushion device. In an embodiment where the method is being conducted in a milking stall, the milking process begins before the inflation of the air cushions and the sensors determine the force being exerted while the milking process occurs.

In one embodiment, the method includes providing an air cushion system installed at a location, positioning an animal on the air cushion device such that each of the animal's hoofs are positioned on an individual air cushion, inflating the air cushion device with the air supply after the animal is positioned, using the sensors to determine a force data for each of the plurality of air cushions while the air cushions are inflated, and determining lameness of the animal based on the force data for each of the air cushions. In this embodiment, the air cushion system is the air cushion system described above.

This device may be used to safely measure lameness and total weight management of animals during the milking process. The device can be used on any animal that might be milked, such as dairy cows, goats, sheep, etc. In this embodiment, the device is designed to be installed directly into the milking stall. The portion of the device exposed to the milking floor is waterproof and airtight, thereby allowing the device to function properly in the wet environment. This device may also be used on animals who are not being milked, but are in a stationary position. This device could also be installed in other areas of the farm such as cattle chutes, horse stalls, or any area on-site where the animal can be contained.

In embodiments that use the device while milking the animal, results are particularly accurate. During the milking process, the animal is maintained in a very still position, as compared to when it is feeding or in a stall. Further, the method can be performed without any added time requirement for the owner because it will be completed while the animal is being milked. This provides an opportunity to detect potential lameness and weight loss before the animal's milk production is affected. Unequal weight distribution can be an indicator of lameness in an animal. Further, the total weight of the animal can be determined by summing all separate force readings.

Due to the waterproof nature of the air cushion device, it is suitable for use in other wet environments such as underwater animal therapy. Further, the device could be used in auto-calf feeding stations to monitor newborn calves weight gain on a daily basis.

Optionally, the computation device will store force data for each animal each time it is measured in a data base. This allows the system to track animal lameness and weight for total weight management and health management. This information may be a cloud-based system such that the operator or manager can access the data and determinations at any time in the field using any number of devices.

It should be understood that while the examples herein and discussion herein focus on lameness determination for four-legged animals, particularly farm animals and animals capable of being milked, the system, device, and methods can be configured to work for any animal and/or human.

DETAILED DESCRIPTION OF THE INVENTION

The present invention relates to a force-measuring system, method, and device for use in determining lameness and total weight management in animals. An embodiment of the force-measuring system and device is illustrated in FIGS. 1-7 and 7A. It should be understood that while the present invention is described herein with specific reference to dairy cows while being milked, the present invention may be incorporated for use with all animals and/or humans. The depictions of the invention should not be in any way considered limited to four legged animals or animals being milked.

Figure 1:
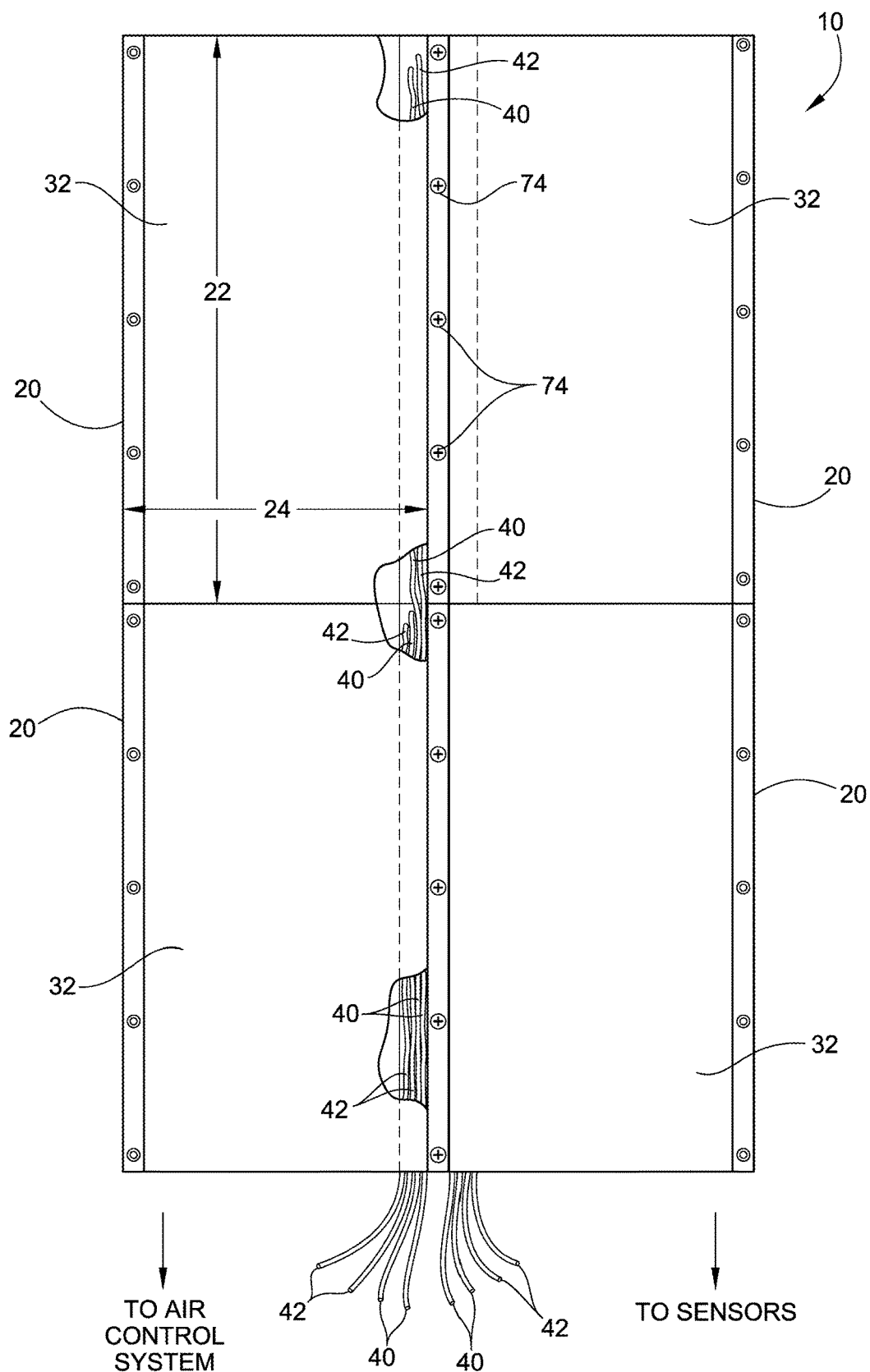
FIG. 1 is a top plan view of an air cushion device for the present invention.
Figure 2:
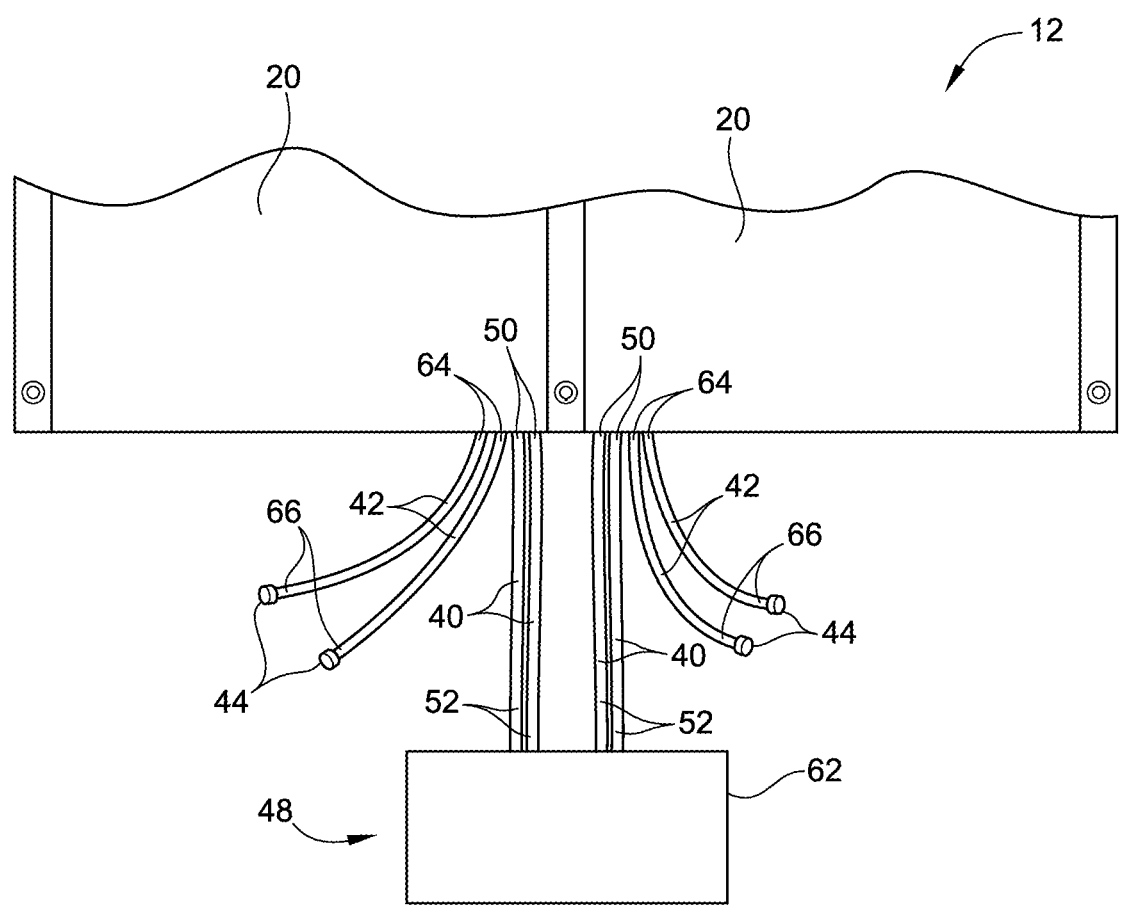
FIG. 2 is a partial top plan view of the air cushion system for the present invention.

Referring to FIGS. 1 and 2, the force-measurement system includes an air cushion device 10 and an air cushion system 12. The air cushion device 10 includes a plurality of air cushions 20, an incoming air line 40 for each air cushion 20 and a data air line 42 for each air cushion 20. The air cushion system 12 includes the air cushion device 10, an air source system 48, and sensors 44. For the air cushion device 10, each air cushion is connected to an incoming air line 40 and a data air line 42. For the air cushion system 12, each incoming air line 40 supplies an air cushion 20 with air to inflate the air cushion 20 with a predetermined amount of air such that each air cushion 20 is inflated with equal amounts of air. Each data air line 42 is connected to a sensor 44. The sensors 44 measure the force exerted on the air pillows 20 once they are inflated. Based on the measurements from the sensors 44, lameness and total weight can be determined. In an embodiment, the air cushion device 10 is waterproof and dust proof. The waterproof air cushion device 10 is capable of use in dusty environments such as barns, animal stalls and is also capable of use in wet environments such as milking stalls and underwater.

Figure 5:
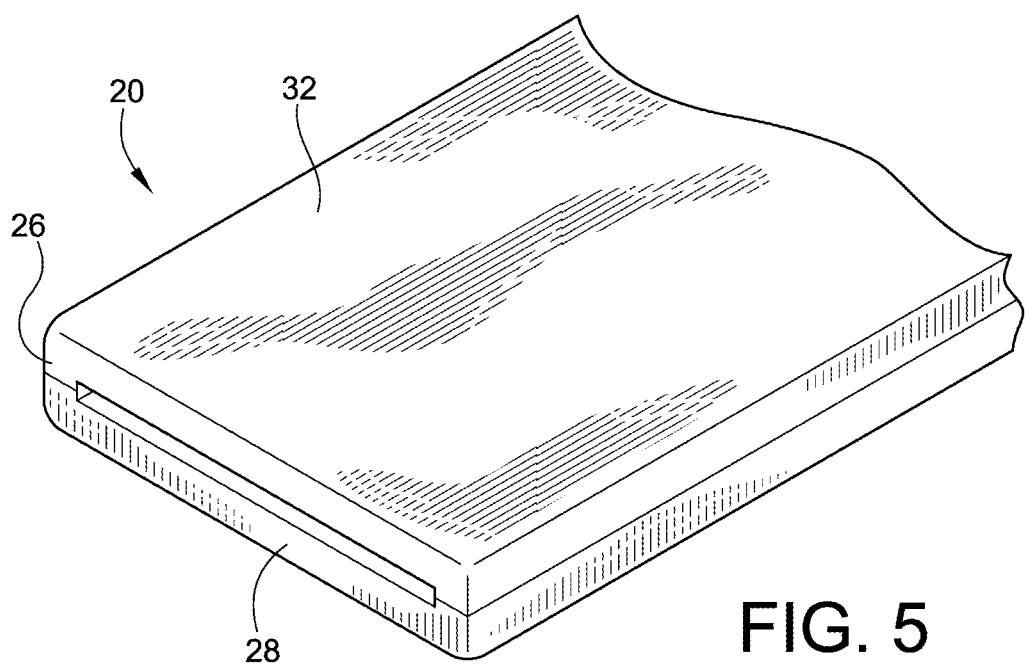
FIG. 5 is a cross section view of an air cushion for the present invention.
Figure 6:
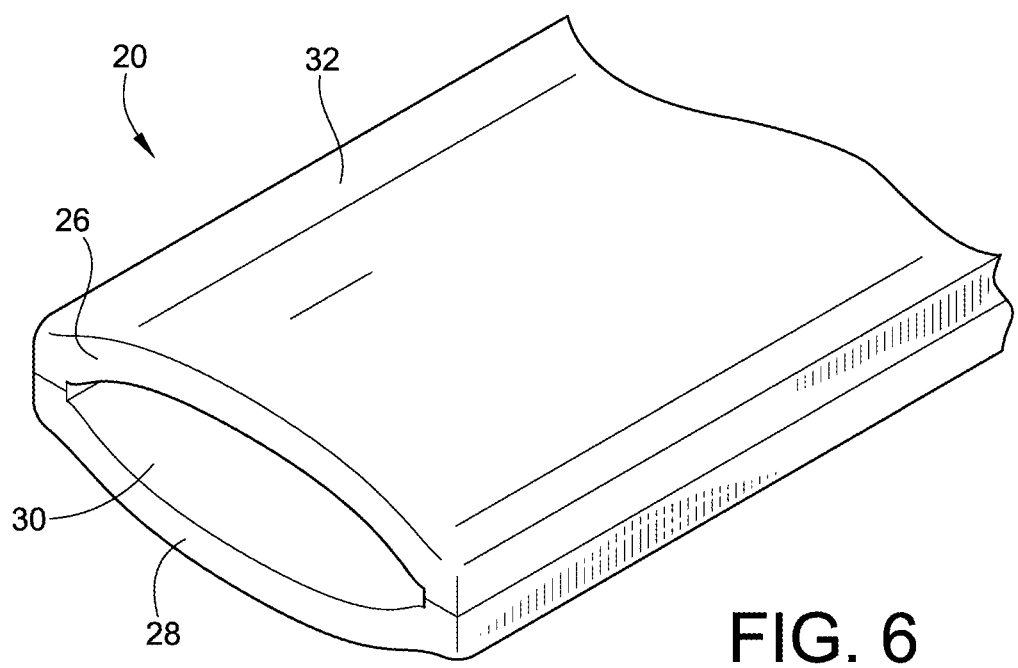
FIG. 6 is a cross section view of an inflated air cushion of FIG. 5.

As illustrated in FIGS. 1 and 2, in an embodiment, each air cushion 20 will be identical and symmetrical. This allows for the air cushions 20 to be interchangeable and reversible, so they can be rotated and/or flipped for even wearing and only the worn air cushion 20 will need to be replaced. In an embodiment, each air cushion 20 is rectangular in shape with each air cushion having the same length 22 and width 24. As illustrated in FIGS. 5 and 6, each air cushion will include a top member 26 and a bottom member 28. In an embodiment, the top member 26 and bottom member 28 are identical, with the top member 26 positioned directly above the bottom member 28. The perimeter of the top member 26 is sealed to the perimeter of the bottom member 28, such that the interior of the top member 26 and the bottom member 28 form an inflatable pocket 30 between the members 26 and 28. The top member 26 and bottom member 28 of the air cushion 20 may each have an outer facing standing surface 32. Optionally, only the top member 26 has an outer facing standing surface 32. The bottom member 28 has no outer facing surface, but it is not a standing surface 32. The perimeter seal will be air-tight and include a connection (not pictured) to the incoming air line 40 and a connection (not shown) to the data air line 42.

The top member 26 and bottom member 28 can be made out of any material suitable for forming the air cushion 20 and sufficient for withstanding the weight and wear of the animals to be tested. The top member 26 and bottom member 28 may be made from a highly durable rubberized material capable of expanding and holding up to 3,000 pounds. In another embodiment, the top member 26 and bottom member 28 may be capable of expanding and holding up to 5,000 pounds. The outer standing surface 32 of the top member 26 and/or bottom member 28 may be textured and/or treated to provide extra traction and prevent the animals from slipping while standing on the air cushions 20. For example, the standing surface 32 may be textured or a non-slip coating may be applied.

Optionally, a rigid platform (not shown) is removably attached to the standing surface 32 of the top member 26 of the air cushion 20. The platform may provide for a more stable standing surface for the animal and enhance the durability of the air cushion 20. The platform may be made out of any material suitable for supporting the weight of the animal to be analyzed. The platform may be made of a highly durable plastic capable of holding up to at least the same weight that the air cushions 20 are configured to hold. The surface of the platform may be of any size provided it is not larger than the flat surface dimension of the air cushion 20 and provided it is large enough to contain one of the animal's feet. The surface of the platform may cover the entire surface of the air cushion 20 to provide an even walking surface for the animal. The platform may be removably attached to the air cushion 20. This may be accomplished by incorporating a hook and loop fastener into the center of the air cushion 20 and the center of the platform to prevent the platform from shifting and/or moving positions during operation. It should be understood that this is merely one way of connecting the platform to the air cushion 20 and any other known way to connect the platform to the air cushion 20 may be employed.

The connections (not pictured) between the air cushion 20 and the incoming air line 40 and between the air cushion 20 and the data air line 42 may be any type of connection that will attach the air lines 40 and 42 to the air cushion 20 in an air-tight manner, such that air can flow from the incoming air line 40 into the air cushion 20 to inflate the pocket 30 of the air cushion 20, and such that air can flow from the pocket 30 of the air cushion 20 out through the data air line 42. The connections between the air lines 40 and 42 and the air cushions 20 may allow the air lines 40 and 42 to be removably connected to the air cushions 20 so that the air cushion 20 can be replaced and/or rotated without replacing/moving the air lines 40 and 42. Alternatively, the connections between the air lines 40 and 42 and the air cushions 20 may maintain the air lines 40 and 42 and the air cushions 20 in a permanent and integrated connection. The connections between the air lines 40 and 42 and the air cushion 20 may be positioned at any point along the perimeter of the air cushion 20. Further, the connection for the incoming air line 40 and the connection for the data air line 42 may be grouped together along the perimeter of the air cushion 20 or positioned separate. In one embodiment, the connections for the air lines 40 and 42 are grouped together in one of the corners of the air cushion 20 such that the air cushions 20 can be positioned with all of the airlines running between the air cushions 20 down the same path. The air lines 40 and 42 can be of any length, provided they are of sufficient length to connect the air source 62 and sensors 44 to the air cushions 20. Further, the connections between the air cushions 20 and air lines 40 and 42 may be all the same type of connections, all different connections, or a combination of types of connections.

Figure 3:
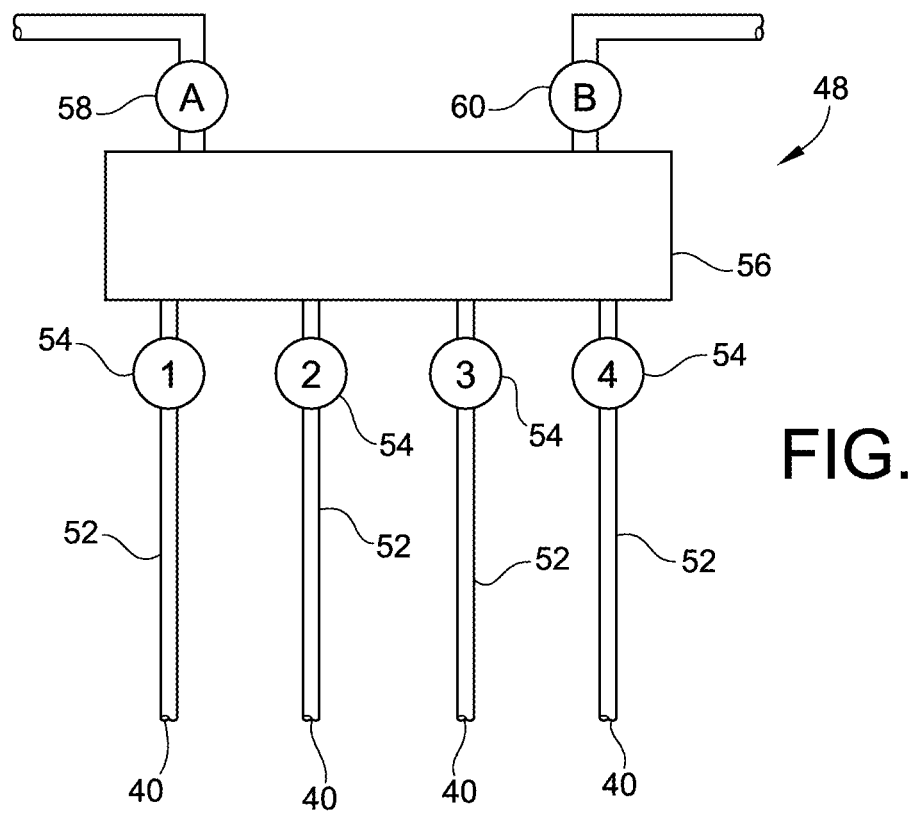
FIG. 3 is a top plan view of an air control system for the air cushion system of FIG. 2.

As illustrated in FIG. 2, the incoming air lines 40 include one end 50 that is connected to the air cushion 20 and a second end 52 that receives the air to inflate each air cushion 20 and is connected to an air source system 48. At minimum, the air source system 48 includes an air source 62 connected to the second end 52 of the incoming air supply lines 40. As illustrated in FIG. 3, in one embodiment, the air source system 48 includes air control switches 54, a main air manifold 56, an air in air control switch 58, an air dump air control switch 60, and an air source 62 (not shown in FIG. 3). The second end 52 of each incoming air line 40 is connected to an air control switch 54. Each air control switch 54 is connected to a main air manifold 56. The main air manifold 56 is connected to an air in air control switch 58 and an air dump air control switch 60. The air in air control switch 58 is connected to an air source 62. The air control switches 54, 58 and 60 operate to allow or prohibit air from moving throughout the system 12, such that when an air control switch is open, air can flow throughout that portion of the system and when the air control switch is closed, air will be prohibited from moving throughout that portion of the system. The air source 62 may constantly be providing air to the system 12, but will only inflate the air cushions 20 when air control switches 58 and 54 are open. Alternately, the air source 62 may be configured to provide air to the system 12 on an as needed basis. The air control switches 54, 58 and 60 can be any type of switch suitable for controlling airflow to that portion of the system 12. One switch option suitable for the air control switches 54, 58, and 60 is air control solenoid valves. It should be understood that the above description merely provides examples of the air supply system 48 and that any combination that includes at least an air source 62 configured to supply air to a plurality of incoming air lines 40 with an ability to trap the air in the air lines can be used. The air source 62 used must be sufficient to inflate the air cushions 20 with the weight of the animal standing on the air cushions with a predetermined amount of air.

Figure 4:
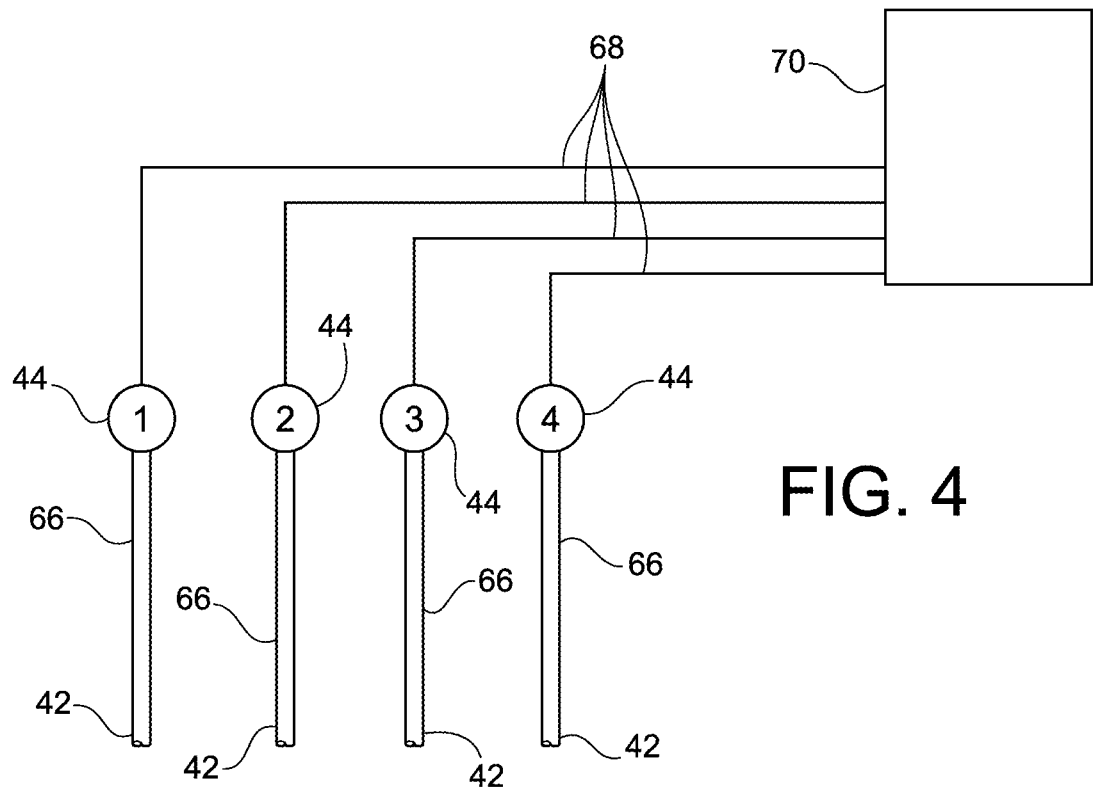
FIG. 4 is a top plan view of the sensors and optional computation system for the air cushion system of FIG. 2.

As illustrated in FIG. 2, each data air line 42 includes one end 64 that is connected to one of the air cushions 20 and a second end 66 connected to a sensor 44 such that the sensor is operatively engaged with the air cushion 20 to detect the force exerted on the air cushion 20 when inflated. The sensor can be any type of sensor capable of detecting vertical forces on the inflated air cushion 20 through the data air line 42. For example, one type sensor suitable for the sensor 44 is an electronic pressure gauge. As illustrated in FIG. 4, the sensors 44 may operably connected to a computation device 70, such as a computer, computerized system, tablet, smart phone, etc. The computation device 70 receives data from the sensors 44 and uses the data to determine lameness and overall weight for the animal. It should be understood that the computation device 70 may be directly connected 68 to the sensors 44 or may be remotely connected to the sensors 44 through a network or other Wi-Fi system or any other way of remotely connecting the computation device 70 to the sensors. Further, there may be intermediate devices connected to the sensors 44 to allow the sensor data to be transferred to the computation system 70. Alternately, it should be understood that the computation device 70 may not be connected to the sensors 44 (directly or through a network) and that the sensors 44 might be read to determine the sensor reading and that reading may be manually input into a computation device 70.

In embodiments for use with four-legged animals, ideally four air cushions 20 will be placed in the layout depicted in FIG. 1, one air cushion 20 per animal foot. In systems for use in milking stalls or other stalls, the air cushions 20 are designed to be attached to and incorporated into the stalls. As illustrated in FIGS. 1 and 2, each air cushion 20 may include connection mechanisms 74, such as eyelet rivets, positioned around the perimeter of the air cushion 20 to allow the air cushions 20 to be installed and replaced at the on-site location. As illustrated in FIG. 7A, the connection mechanisms 74 may be contained on a flap 31 connected to the body of the air cushion 20. The flap 31 may be removably attached to the air cushion 20. Alternatively, the flap 31 may be non-removably attached and integrated into the air cushion 20. For example, the flap 31 could be the top member 26 of the air cushion 20, extended past the width 24 of the bottom member 28 of the air cushion 20. The flap 31 may extend past the body of the air cushion on either side of the width 24 of the air cushion 20 or on just one side. As further illustrated in FIG. 7A, the flaps 31 of each air cushion may be configured such that when the air cushions 20 are configured as a pair, the flaps 31 of paired air cushions 20 overlay each other and the connection mechanisms 74 on the flap 31 of one air cushion 20 are positioned to line up with the connection mechanisms 74 on the flap 31 of a paired air cushion 20 such that a bolt 75 can be passed through the corresponding connection mechanisms 74 of each air cushion 20 and affix the air cushions 20 in place at the location of installation.

Figure 7:
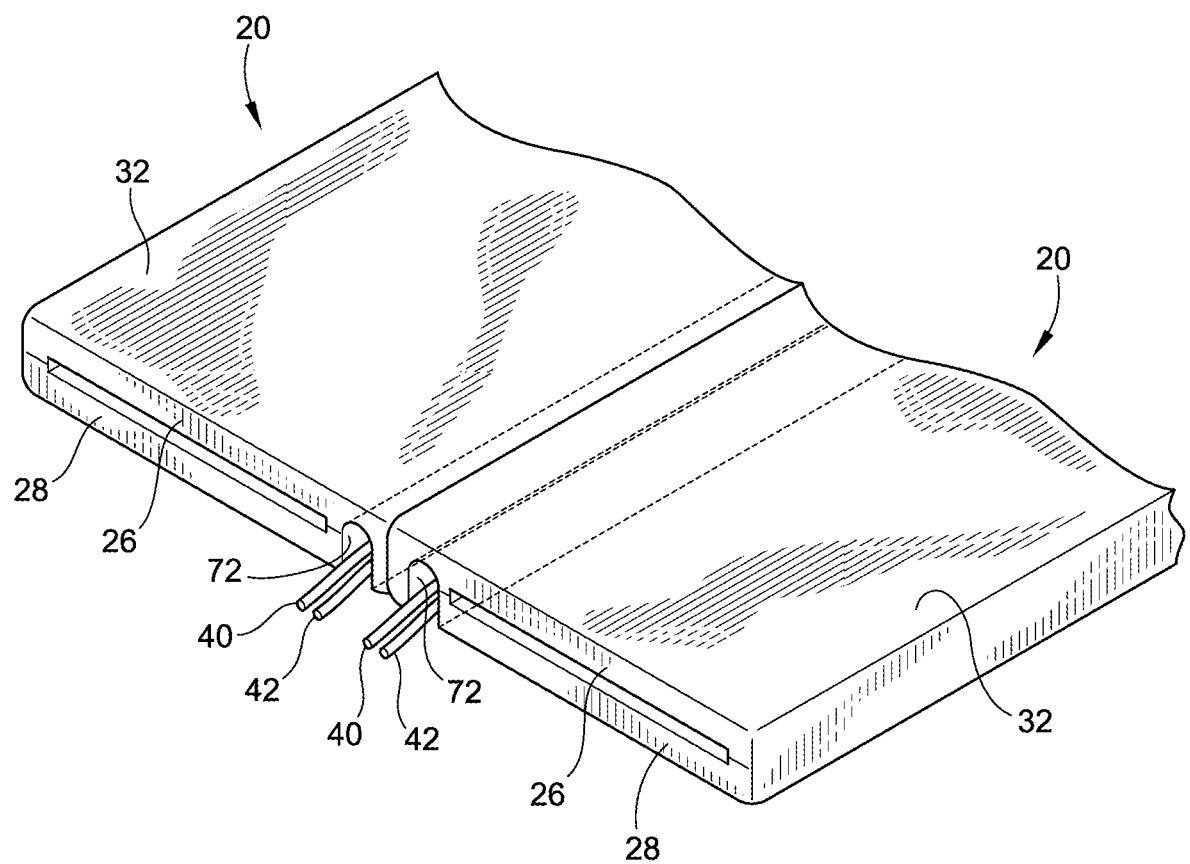
FIG. 7 is a cross section view of two air cushions installed with a tunnel system for air tube organization of the present invention.
Figure 7A:
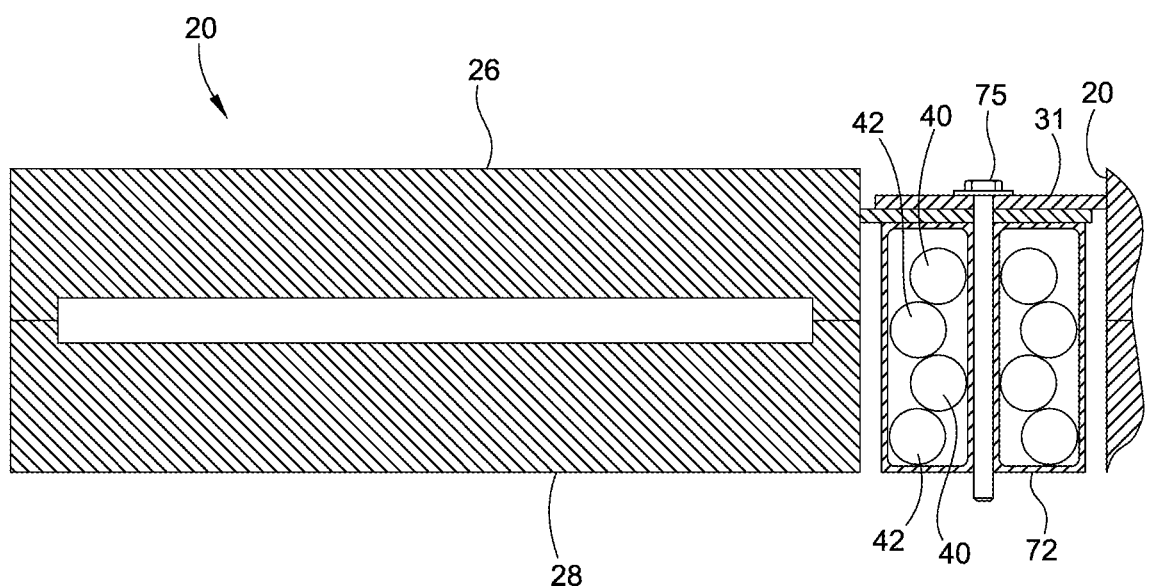
FIG. 7A is a partial cross section view of an air cushion device installed with an alternate tunnel system for air tube organization of the present invention.

As illustrated in FIGS. 7 and 7A, the air cushions may include a rigid semi-circular or rectangular elongated tunnel 72 running along the perimeter of the air cushion 20. The elongated tunnels 72 allow for routing the incoming air lines 40 and data air lines 42 out of the configuration of air cushions 20 and protect the air lines 40 and 42 from being pinched or flattened by the animal or by the inflation of the air cushions 20. The elongated tunnels 72 may be removably attached to the air cushion 20 such that they can be added and configured for the number of air cushions that are required to route air lines 40 and 42. For example, where there are four air cushions 20 configured as shown in FIG. 1, and where the connections for the air lines 40 and 42 all meet in the center corners, only the bottom two air cushions 20 might require the elongated tunnels 72. This is merely an example of routing the air lines 40 and 42, and other embodiments are contemplated where the air lines 40 and 42 are routed in opposite directions or where the air lines 40 and 42 are routed along the width 24 of the air cushions 20, rather than the length. Like the version illustrated in FIG. 7A, in versions of the air cushions 20 that include flaps 31, the elongated tunnels 72 are configured to be positioned under the lowest of the overlapping flaps 31 with one tunnel 72 positioned along the length 22 of each air pillow 20 with the bolt 75 inserted in between the tunnels 72. This provides additional strength to the tunnels 72 to keep them from collapsing.

In embodiments where the air cushion device 10 is waterproof, the air lines 40 and 42 for the air cushion device 10 will be sufficiently long enough such that the remainder of the air cushion system 12 components, including any electronic devices such as the air source system 48, sensors 44, and computation device 70, will be removed from the wet environment. For example, the air source system 48 and sensors 44 may be contained in a cabinet or other device at a sufficient distance from the wet environment of the milking stall.

Figure 8:
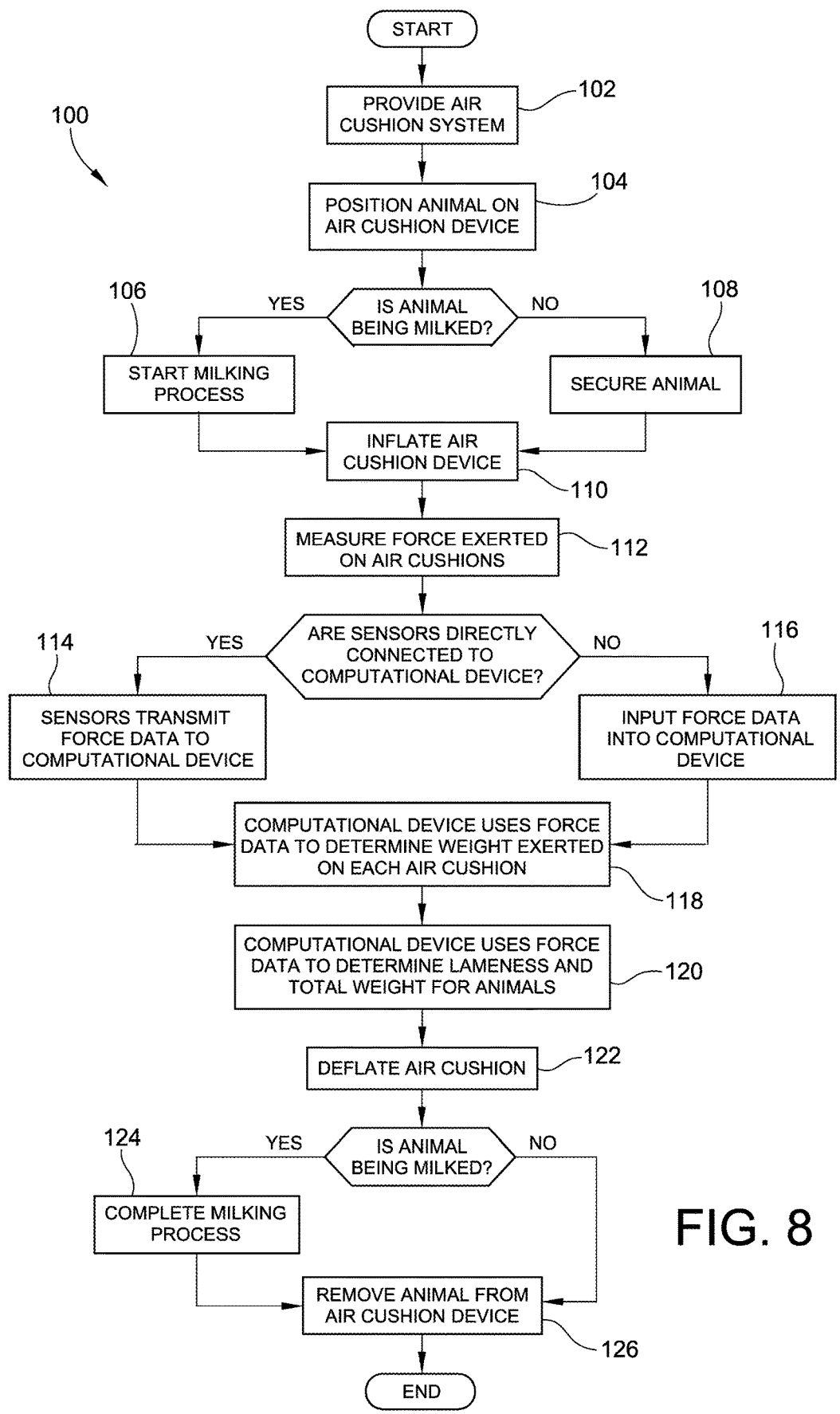
FIG. 8 is a flow chart of a method for determining lameness and total weight in an animal of the present invention.

FIG. 8 depicts a flowchart of an exemplary embodiment of method 100 for determining lameness in an animal.

At step 102, a properly configured air cushion system 12 is installed. It is preferred that the air cushion system 12 be installed at an on-site location such as a milking stall. However, the air cushion system will work at any site. At step 104, an animal is positioned on the air cushion device such that each air cushion has one animal foot positioned on it. In air cushion systems where the device is installed in a milking stall, at step 106, the milking process is initiated. In air cushion systems where the device is not installed in a milking stall, at step 108, the animal is secured on the air cushion device. For example, if the air cushion device is installed in a cattle chute, the cow is secured in the cattle chute.

At step 110, the air cushions are inflated with the air control system. In an embodiment, each air cushion is inflated with a predetermined amount of air. Once the air cushions are inflated, at step 112, the sensors measure the force being exerted on each air cushion. In air cushion systems where the sensors are connected to a computation device, at step 114, the sensors transmit the force data to the computation device. The computation device may be directly connected to the sensors or the computation device may be remotely connected to the sensors. Further, there may be intermediate devices between the computation device and the sensors facilitating the transfer of the data collected by the sensors. In air cushion systems where the sensors are not connected to a computation device, at step 116 the sensors are read and the data is input into a computation device.

At step 118, the computation device uses the force data from the sensors to determine the weight exerted on each air cushion. At step 120, the computation device uses the force data from the sensors to determine lameness in the animal and to determine the total weight of the animal. Optionally, the computational device stores the force data and determinations in a system database for review and further analysis.

At step 122 the air cushions are deflated. It should be understood that this step can occur any time after the data from the sensors is recorded at step 114 or 116. At step 124, for methods performed while the animal is being milked, the milking process is completed. At step 126, the animal is removed from the air cushion device. It should also be understood that steps 124 and 126 can occur after the computations, while the computations are being determined, or before the computations are performed.

Figure 9:
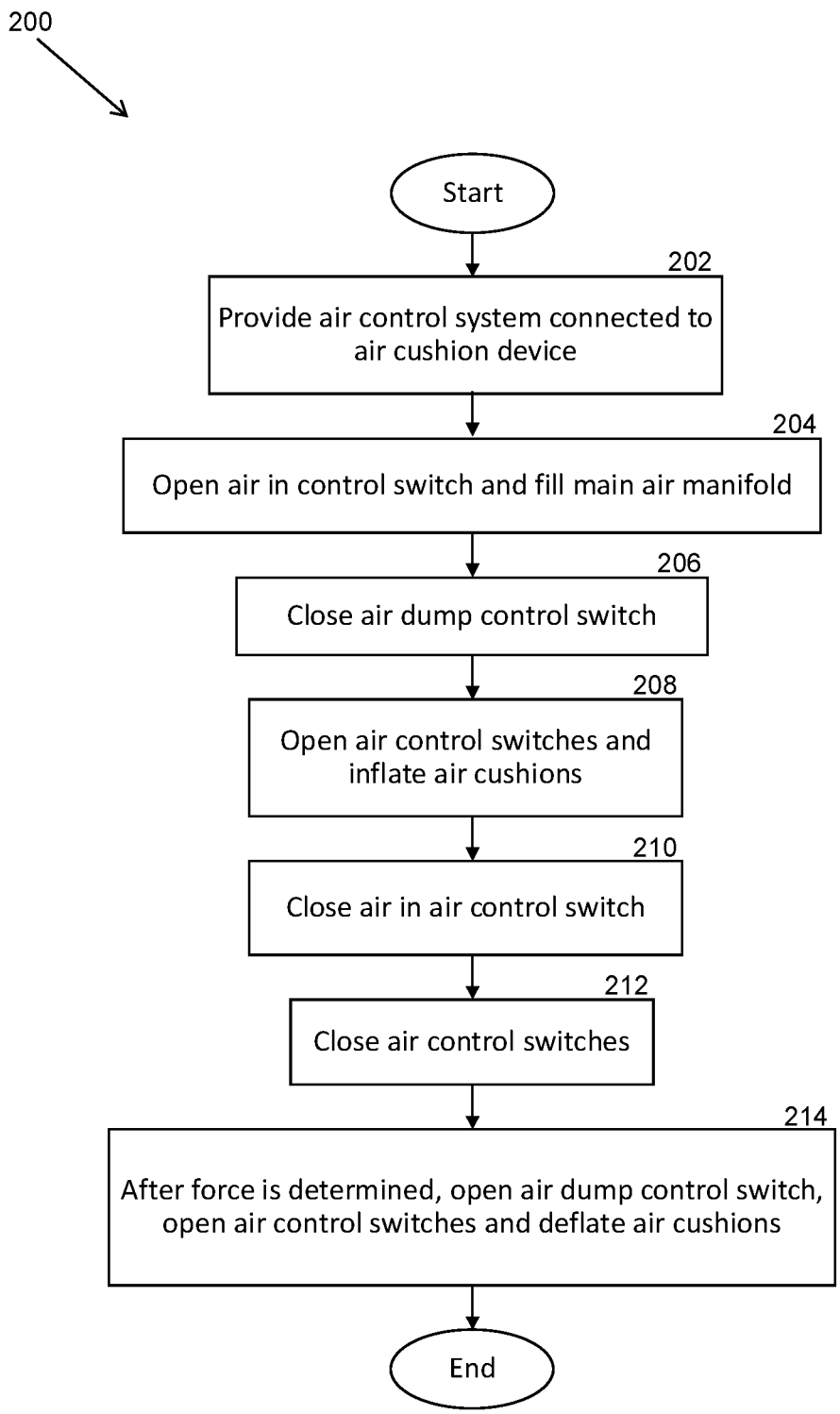
FIG. 9 is a flow chart of a method for operating the air cushion system of FIG. 2 with an air control system of FIG. 3.

FIG. 9 depicts an exemplary embodiment of method 200 for inflating the air cushions.

At step 202, an air source connected to an air control system as shown in FIG. 3 is provided, the air control system being connected to an air cushion device as shown in FIG. 2. The air source may be always on or turned on prior to inflating. At step 204, the air in control switch is opened and the main air manifold is filled. At step 206, the air dump control switch is closed. It should be understood that steps 204 and 206 may occur simultaneously, near simultaneously, or in reverse order. At step 208, the air control switches are opened and the air cushions are inflated with a predetermined amount of air. At step 210, the air in air control switch is closed. At step 212, once the pressure is distributed among the incoming air lines, the air control switches are closed. At step 214, once the sensors have determined the force being exerted and the data is read, the air dump control switch is opened, the air control switches are opened, and the air cushions are deflated.

Directional terms, such as "top," "upper," "bottom," "lower," "outward," "inward," "end," etc., are used for convenience in referring to the accompanying pictures. In general, the directional terms refer to a direction on the invention in relation to position and placement on the invention.

Any version of any component or method step of the invention may be used with any other component or method step of the invention. The elements described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference in their entirety to the same extent as if each individual reference were specifically and individually indicated as being incorporated by reference. In case of conflict between the present disclosure and the incorporated references, the present disclosure controls.

The devices, methods, compounds and compositions of the present invention can comprise, consist of, or consist essentially of the essential elements and limitations described herein, as well as any additional or optional steps, ingredients, components, or limitations described herein or otherwise useful in the art.

While this invention may be embodied in many forms, what is described in detail herein is a specific preferred embodiment of the invention. The present disclosure is an exemplification of the principles of the invention and it is not intended to limit the invention to the particular embodiments illustrated. It is to be understood that this invention is not limited to the particular examples, process steps, and materials disclosed herein as such process steps and materials may vary somewhat. It is also understood that the terminology used herein is used for the purpose of describing particular embodiments only and is not intended to be limiting, since the scope of the present invention will be limited to only the appended claims and equivalents thereof.

It is to be understood that the following claims are exemplary in nature only, and do not and should not be interpreted to place any limitations on any claims in any subsequent applications whatsoever.

It is also to be understood that the subsequent specification appendix provides exemplary aspects of the present invention and does not and should not be interpreted to place any limitations on any subsequent applications whatsoever. This written description uses examples to disclose the invention, including the best mode, and also to enable any person skilled in the art to make anew the invention. Any dimensions or other size descriptions are provided for purposes of illustration and are not intended to limit the scope of the claimed invention. Additional aspects can include slight variations, as well as greater variations in dimensions as required for use in the industry. The patentable scope of the invention may include other examples that occur to those skilled in the art.

What is claimed is:

1. An air cushion device for determining lameness and total weight management in animals, the device comprising:
    a plurality of air cushions, each air cushion including a top member and a bottom member connected by an airtight seal between the top member and the bottom member along a perimeter of the air cushion, each air cushion further includes an expandable air pocket formed in the air cushion by the airtight seal, wherein each air cushion is configured to receive at least a portion of an animal on the top member, further wherein the expandable air pocket of each air cushion is connected to an incoming air line and a data air line;
    a plurality of incoming air lines, each incoming air line connected to the expandable air pocket of one of the plurality of air cushions, wherein the incoming air lines supply each air cushion with a supply of air to inflate each air cushion; and
    a plurality of data air lines, each data air line connected to the expandable air pocket of one of the plurality of air cushions, wherein the data air lines supply a force being exerted on each of the plurality of air cushions once the air cushions are inflated.

2. The air cushion device of claim 1, wherein all components of the air cushion device are waterproof.

3. The air cushion device of claim 1, wherein each of the plurality of air cushions includes a plurality of connection mechanisms positioned around the perimeter of each air cushion, wherein the plurality of connection mechanisms facilitate installation and configuration of the air cushion device.

4. The air cushion device of claim 3, wherein the air cushion device is configured to be installed in a milking stall.

5. The air cushion device of claim 1, the air cushion device further including a plurality of elongated tunnels connected to the perimeter of each of the plurality of air cushions, wherein the plurality of elongated tunnels are configured to allow for routing of the plurality of incoming air lines and the plurality of data air lines.

6. The air cushion device of claim 1, wherein each air cushion of the plurality of air cushions further includes a rigid standing platform removably attached to an outer surface of the top member of the air cushion, wherein the rigid standing platform is smaller in surface area than the outer surface of the top member, further wherein the rigid standing platform is configured to receive at least a portion of the animal.

7. The air cushion device of claim 1, wherein each expandable air pocket of each air cushion of the plurality of air cushions is configured to be expanded with a predetermined amount of air while the animal is standing on the air cushions, further wherein each air cushion is configured to withstand the weight of the animal while in the expanded state.

8. An air cushion system for determining lameness and total weight management in animals, the system comprising:
    an air cushion device, the air cushion device including:
        a plurality of air cushions, each air cushion including a top member and a bottom member connected by an airtight seal between the top member and the bottom member along a perimeter of the air cushion, each air cushion further includes an expandable air pocket formed in the air cushion by the airtight seal, wherein each air cushion is configured to receive at least a portion of an animal on the top member, further wherein the expandable air pocket of each air cushion is connected to an incoming air line and a data air line,
        a plurality of incoming air lines, each incoming air line connected to the expandable air pocket of one of the plurality of air cushions, wherein the incoming air lines supply each air cushion with a supply of air to inflate each air cushion, and
        a plurality of data air lines, each data air line connected to the expandable air pocket of one of the plurality of air cushions, wherein the data air lines supply a force being exerted on each of the plurality of air cushions once the air cushions are inflated;
    an air supply system connected to the plurality of incoming air lines of the air cushion device, the air supply system including an air supply to provide air to the air cushion device; and
    a plurality of sensors connected to the plurality of data air lines of the air cushion device to determine the force being exerted on the air cushions, wherein a number of sensors equals a number of data air lines, further wherein the sensors are connected to the data air lines on a one-to-one basis.

9. The air cushion system of claim 8, wherein the air supply system further includes a plurality of air control switches connected between the air supply and the plurality of incoming air lines, wherein a number of air control switches equals a number of incoming air lines, further wherein the air control switches are connected to the incoming air lines on a one-to-one basis, further wherein the air control switches are configured to control the supply of air to the air cushion device.

10. The air cushion system of claim 9, wherein the air supply system further includes a main air manifold connected between the air supply and the plurality of air control switches, wherein the main air manifold receives the air from the air supply and facilitates distribution of the air to each of the incoming air lines through each of the air control switches.

11. The air cushion system of claim 10, wherein the air supply system further includes an air in control switch connected between the air supply and the main air manifold, wherein the air in control switch is configured to control the supply of air from the air supply to the main air manifold.

12. The air cushion system of claim 9, wherein the air supply system further includes an air dump control switch connected to the main air manifold, wherein the air dump control switch controls a release of air from the air cushion device after the air cushion device has been inflated.

13. The air cushion system of claim 8, the system further including a computation device operatively connected to the plurality of sensors, wherein the computation device is configured to receive data from the plurality of sensors.

14. The air cushion system of claim 13, wherein the computation device is operatively connected to the sensors through a physical data connection.

15. The air cushion system of claim 13, wherein the computation device is operatively connected to the sensors through a wireless connection.

16. A method for determining lameness and total weight, the method comprising:
providing an air cushion system installed at a location, wherein the air cushion system includes:
an air cushion device, the air cushion device including:
a plurality of air cushions, each air cushion including a top member and a bottom member connected by an airtight seal between the top member and the bottom member along a perimeter of the air cushion, each air cushion further includes an expandable air pocket formed in the air cushion by the airtight seal, wherein each air cushion is configured to receive at least a portion of an animal on the top member, further wherein the expandable air pocket of each air cushion is connected to an incoming air line and a data air line,
a plurality of incoming air lines, each incoming air line connected to the expandable air pocket of one of the plurality of air cushions, wherein the incoming air lines supply each air cushion with a supply of air to inflate each air cushion, and
a plurality of data air lines, each data air line connected to the expandable air pocket of one of the plurality of air cushions, wherein the data air lines supply a force being exerted on each of the plurality of air cushions once the air cushions are inflated,
an air supply system connected to the plurality of incoming air lines of the air cushion device, the air supply system including an air supply to provide air to the air cushion device, and
a plurality of sensors connected to the plurality of data air lines of the air cushion device to determine the force being exerted on the air cushions, wherein a number of sensors equals a number of data air lines, further wherein the sensors are connected to the data air lines on a one-to-one basis;
positioning an animal on the air cushion device, wherein each of the animal's hoofs are positioned on an individual air cushion;
inflating the air cushion device with the air supply after the animal is positioned;
using the sensors to determine a force data for each of the plurality of air cushions while the air cushions are inflated; and
determining lameness of the animal based on the force data for each of the air cushions.

17. The method of claim 16, wherein the location of installation of the air cushion system is a milking stall.

18. The method of claim 17, the method further including starting a milking process for the animal prior to inflating the air cushion device.

19. The method of claim 18, the method further including finishing the milking process for the animal after determining the force data for each of the plurality of air cushions.

20. The method of claim 16, wherein the sensors are operationally connected to a computation device, the method further including transmitting, by the sensors, the force data to the computation device, wherein the computation device performs the determination of lameness.

* * * * *